US007175633B2

(12) United States Patent
Roth et al.

(10) Patent No.: US 7,175,633 B2
(45) Date of Patent: Feb. 13, 2007

(54) ORTHOPEDIC IMPLANT INSERTION INSTRUMENTS

(75) Inventors: Christoph A. Roth, West Chester, PA (US); Charles E. Geltz, Drexel Hill, PA (US); Frank A. Wilson, Essington, PA (US)

(73) Assignee: Synthes (USA), West Chester, PA (US)

(*) Notice: Subject to any disclaimer, the term of this patent is extended or adjusted under 35 U.S.C. 154(b) by 452 days.

(21) Appl. No.: 10/269,976

(22) Filed: Oct. 15, 2002

(65) Prior Publication Data

US 2003/0074005 A1 Apr. 17, 2003

Related U.S. Application Data

(60) Provisional application No. 60/329,536, filed on Oct. 17, 2001.

(51) Int. Cl.
*A61B 17/62* (2006.01)

(52) U.S. Cl. .......................... 606/99; 606/98; 606/104

(58) Field of Classification Search ................ 606/102, 606/99, 53, 96–97
See application file for complete search history.

(56) References Cited

U.S. PATENT DOCUMENTS

| | | | | |
|---|---|---|---|---|
| 4,599,999 | A | 7/1986 | Klaue | 128/92 |
| 4,719,907 | A | 1/1988 | Banko et al. | 128/92 |
| 4,862,883 | A | 9/1989 | Freeland | 128/92 |
| 4,911,153 | A | 3/1990 | Border | 606/98 |
| 4,955,885 | A | 9/1990 | Meyers | 606/53 |
| 5,030,221 | A | 7/1991 | Buechel et al. | 606/91 |
| 5,042,983 | A | 8/1991 | Rayhack | 606/87 |
| 5,049,150 | A | 9/1991 | Cozad | 606/86 |
| 5,180,388 | A | 1/1993 | DiCarlo | 623/16 |
| 5,261,915 | A | 11/1993 | Durlacher et al. | 606/85 |
| 5,295,991 | A | 3/1994 | Frigg | 606/62 |
| 5,306,278 | A | 4/1994 | Dahl et al. | 606/96 |
| 5,308,350 | A | 5/1994 | Mikhail | 606/88 |
| 5,312,412 | A | 5/1994 | Whipple | 606/96 |
| 5,334,203 | A | 8/1994 | Wagner | 606/61 |
| 5,346,496 | A | 9/1994 | Pennig | 606/96 |
| 5,352,228 | A * | 10/1994 | Kummer et al. | 606/64 |
| 5,403,320 | A | 4/1995 | Luman et al. | 606/89 |
| 5,403,322 | A | 4/1995 | Herzenberg et al. | 606/98 |

(Continued)

FOREIGN PATENT DOCUMENTS

WO WO 92/01422 7/1991

*Primary Examiner*—Eduardo C. Robert
*Assistant Examiner*—D. Jacob Davis
(74) *Attorney, Agent, or Firm*—Jones Day

(57) ABSTRACT

Orthopedic implant insertion instruments for precision guiding of a fracture fixation implant into fractured bone to promote healing are disclosed. The implant insertion instruments comprise an insertion handle for implantation of a first fixation implant, an aiming arm for precise guiding of a second fixation implant into bone, a guide sleeve for protection of soft tissue and for translational and rotational control of the second fixation implant, and a drive shaft with coupling screw for attachment to the second fixation implant and for driving the second fixation element through the aiming arm and guide sleeve into the fractured bone. The implant insertion instruments also include a soft tissue clearance device to aid the surgeon in inserting the first fixation implant into the fractured bone. Also disclosed is a measuring device that reduces measuring errors made by a user and a measuring device that determines implant length, diameter, and angle of insertion.

30 Claims, 9 Drawing Sheets

40
50
120
60
70

U.S. PATENT DOCUMENTS

| | | | | |
|---|---|---|---|---|
| 5,429,641 | A * | 7/1995 | Gotfried | 606/67 |
| 5,458,600 | A | 10/1995 | Stapert et al. | 606/63 |
| 5,470,335 | A | 11/1995 | Du Toit | 606/73 |
| 5,489,284 | A | 2/1996 | James et al. | 606/62 |
| 5,498,265 | A | 3/1996 | Asnis et al. | 606/73 |
| 5,499,986 | A | 3/1996 | Dimarco | 606/104 |
| 5,569,262 | A | 10/1996 | Carney | 606/96 |
| 5,576,194 | A | 11/1996 | Chan | 623/16 |
| 5,613,971 | A | 3/1997 | Lower et al. | 606/96 |
| 5,624,447 | A | 4/1997 | Myers | 606/96 |
| 5,681,318 | A | 10/1997 | Pennig et al. | 606/98 |
| 5,722,978 | A | 3/1998 | Jenkins, Jr. | 606/87 |
| 5,728,128 | A | 3/1998 | Crickenberger et al. | 606/97 |
| 5,855,579 | A | 1/1999 | James et al. | 606/151 |
| 5,899,908 | A | 5/1999 | Kuslich et al. | 606/96 |
| 5,904,685 | A | 5/1999 | Walawalkar | 606/73 |
| 5,913,860 | A | 6/1999 | Scholl | 606/100 |
| 5,951,561 | A | 9/1999 | Pepper et al. | 606/80 |
| 5,989,260 | A | 11/1999 | Yao | 606/102 |
| 6,015,408 | A | 1/2000 | Pichon et al. | 606/53 |
| 6,024,746 | A | 2/2000 | Katz | 606/88 |
| 6,027,507 | A | 2/2000 | Anderson et al. | 606/12 |
| 6,033,407 | A | 3/2000 | Behrens | 606/62 |
| 6,080,159 | A | 6/2000 | Vichard | 606/64 |
| 6,126,659 | A | 10/2000 | Wack | 606/96 |
| 6,126,661 | A | 10/2000 | Faccioli et al. | 606/64 |
| 6,168,595 | B1 * | 1/2001 | Durham et al. | 606/64 |
| 6,174,335 | B1 | 1/2001 | Varieur et al. | 623/22.12 |
| 6,183,477 | B1 | 2/2001 | Pepper | 606/104 |

* cited by examiner

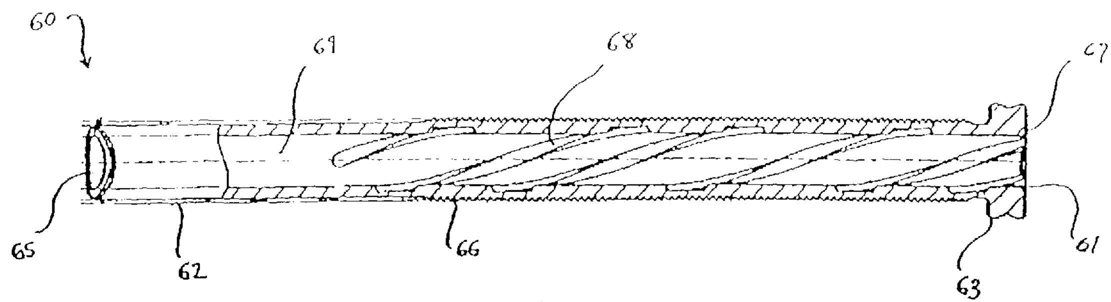
Figure 13
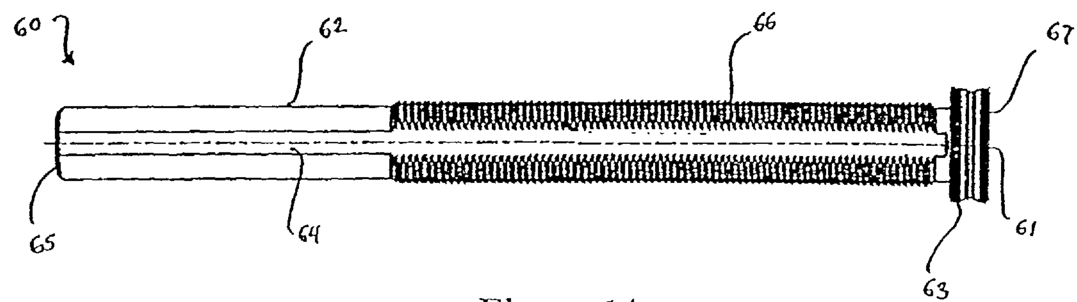
Figure 14
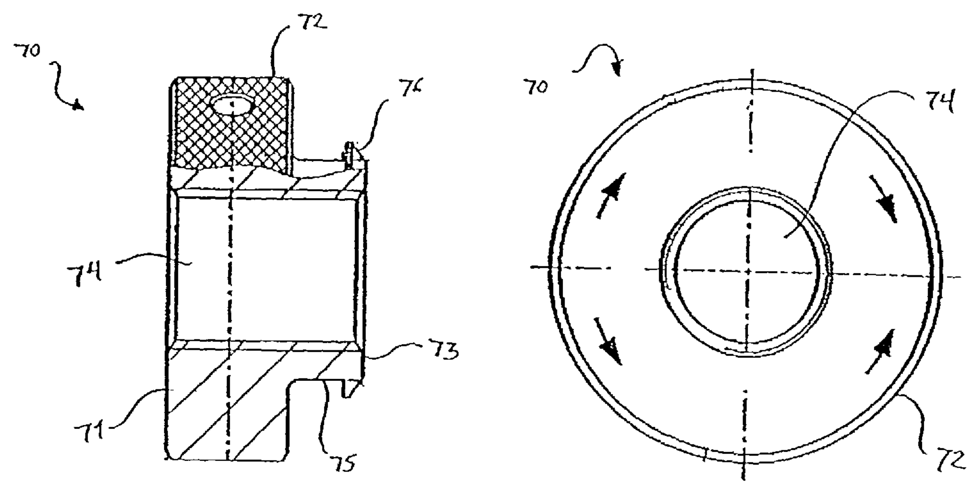
Figure 15
Figure 16

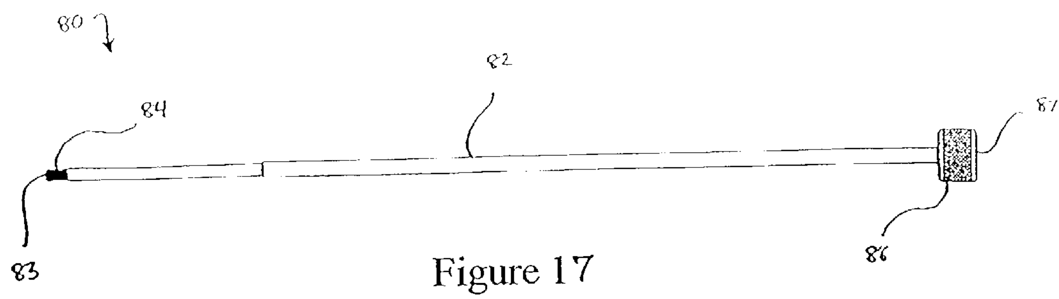
Figure 17
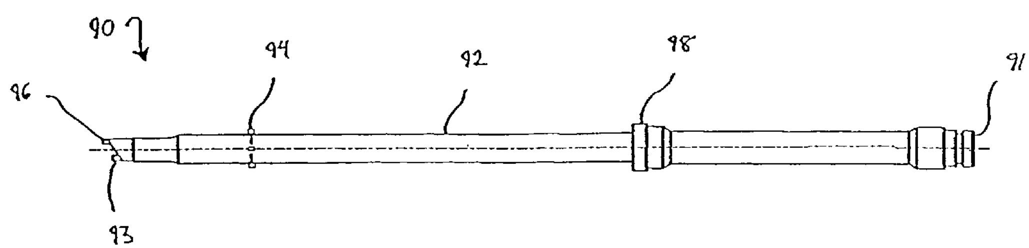
Figure 18
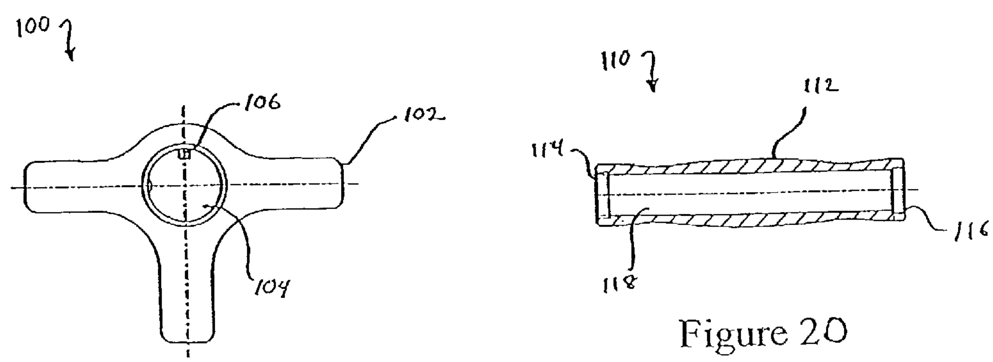
Figure 20
Figure 19

ORTHOPEDIC IMPLANT INSERTION INSTRUMENTS

CROSS-REFERENCE TO RELATED APPLICATIONS

The present application is related to U.S. patent application Ser. No. 09/978,002, entitled "Bone Fixation System" filed on Oct. 17, 2001, and claims priority to provisional patent application No. 60/329,536 filed on Oct. 17, 2001. The entire contents of both of these applications is expressly incorporated herein by reference thereto.

FIELD OF THE INVENTION

This invention relates in general to the treatment of bone fractures, and more particularly, to an orthopedic implant insertion system for improving guidance and placement of a fracture fixation implant into fractured bone to promote healing.

BACKGROUND OF THE INVENTION

Skeletal fractures are common injuries. These fractures are typically debilitating and often require the patient to undergo surgery. Depending on the severity of the fracture, the orthopedic surgeon has several options for treatment, ranging from simple fracture reducing implants to complete prosthetic replacements. However, even when the treatment of the fracture does not call for a complicated procedure such as complete replacement, the proper setting of a fractured bone can still pose substantial challenges to even the most skilled orthopedic surgeon.

The difficulties that a surgeon has to deal with when reducing a fracture are well-known. These difficulties include dealing with the shape and positioning of the bones or bone fragments when aligning the fracture and the accompanying complications regarding the proper placement of an orthopedic implant for supporting and holding the fracture in proper alignment until it heals. This latter problem of implant alignment still remains as one of the challenges facing an orthopedic surgeon in fracture surgery.

For example, fractures which occur in the femur, and especially in the femoral neck and intertrochanteric regions, have traditionally been treated by inserting a nail, such as an intramedullary nail, along the longitudinal axis of the femur and by inserting a second fixation implant, such as a locking implant, from the side of the femur, through the femoral neck, via the intramedullary nail, and into the femoral head. The fixation implant may then be locked to the intramedullary nail and they cooperate to align and compress the bone fragments. However, in order for the fixation implant to be properly implanted in the femoral head, the implant must be aligned prior to insertion through the femur. This is the challenge orthopedic surgeons face with during fracture surgery.

A variety of alignment systems have been developed to facilitate orthopedic implant placement in bone fracture surgery. The use of such alignment systems have substantially assisted orthopedic surgeons in aligning and implanting fixation implants to insure the proper healing of the fracture. However, the previous alignment systems have not been able to accurately predict insertion depth and translational distance and, more importantly, have not been able to accurately predict rotational distance and orientation. Accordingly, there exists a need for improved fixation implant systems.

SUMMARY OF THE INVENTION

The present invention relates to orthopedic implant insertion instruments for precision guiding of a fracture fixation implant into fractured bone to promote healing. The implant insertion instruments comprise a handle member for implantation of a first fixation implant (or a first portion of an implant), at least one arm member for precise guiding of a second fixation implant (or a second portion of the implant) into bone, a sleeve member for protection of soft tissue and for translational and rotational control of the second fixation implant, a nut member for engaging the sleeve member, and a drive shaft with coupling member for attachment to the second fixation implant and for driving the second fixation implant through the arm member and sleeve member into the fractured bone. The implant insertion instruments also include a striking member to aid the surgeon in inserting the first fixation implant into the fractured bone. Also included is a measuring device that reduces measuring errors made by a user and a measuring device that determines implant length, diameter, and angle of insertion.

In general, the handle member is used during the orthopedic procedure to insert a fixation implant into a bone and to connect to the other implant insertion instruments, such as an aiming arm. The handle member is a curved body which may have a bore located at a first end of the handle for coupling to a fixation implant and may have a plurality of bores located at a second end of the handle.

Generally speaking, the arm member is used during orthopedic surgery as an aiming structure for precise positioning of a locking implant. The arm member may have an attachment member and an alignment member located at a first end of the arm member for coupling to the second end of the handle member and may have a sleeve retaining portion located at a second end of the aiming arm member wherein the sleeve retaining portion has an angled bore that is angled with respect to the longitudinal axis of the arm member.

In general, the sleeve member is used during orthopedic surgery to align and guide the locking implant and to protect surrounding soft tissue when a locking implant is implanted into a bone. The sleeve member is slideably inserted into the angled bore of the arm member and may have threading disposed at least partially along an outer surface. In addition, the sleeve member may also have a central bore with at least one helically oriented groove extending substantially along the length of the central bore or have a central bore with at least one pin.

Generally speaking, the nut is used during orthopedic surgery to restrict the insertion depth of a locking implant and to provide compression or reduction to a fracture. The nut may have a threaded bore for threadably attaching to the sleeve member and may have a flange for attaching to the angled bore of the arm member.

The orthopedic implant insertion instruments may also include a striking member for attachment to the handle member. In general, the striking member can be used during intra-operation to help surgeons apply an impact force to the handle member helping drive an implant further into a bone by providing a large impact site clear of any soft tissue. The striking member may have an enlarged end cap with a shaft coupled to a base member, wherein the base member can be fixedly attached to the handle member.

In addition, the orthopedic implant insertion instruments may also include implant driving instruments. The implant driving instruments include, but are not limited to, a drive shaft, a coupling member, an alignment guide, and a handle cover.

In general, the drive shaft is used during orthopedic surgery to couple to a locking implant and help drive the locking implant into the bone. The drive shaft may be cannulated and may have at least one pin or groove located on the body of the drive shaft and a structure located on one end of the drive shaft for attachment to a locking implant.

Generally speaking, the coupling member is also used during orthopedic surgery to couple to a locking implant and help drive the locking implant into the bone. The coupling member has an elongated body with threading disposed on one end for attachment to a locking implant. Furthermore, the coupling member is configured and dimensioned for slideable insertion within the drive shaft.

The implant driving instruments may also include a handle cover for coupling to the drive shaft and an alignment indicator for coupling to the drive shaft for determining the rotational orientation of the drive shaft.

Furthermore, the orthopedic implant insertion instruments may also include an orthopedic implant measurement device and an error reducing measurement device to determine implant dimensions and insertion angles and depths.

The measurement device can be used generally during pre-operation to help surgeons determine the dimensions of the orthopedic implant needed to address a fracture or impending fracture that may be present in an affected bone. The measurement device can further help surgeons determine additional orthopedic measurements such as relative bone fragment angles and, in the case of bones like the femur, the angle of the femoral neck or the angle of equivalent bony structure. The orthopedic implant measurement device has an elongated body with a set of scaled notches disposed partially along a side of the body for determining an implant length. The measurement device also has a set of scaled tabs disposed partially along a side of the body for determining an implant diameter. In addition, the measurement device has an angled set of grooves disposed across the body for determining an angle for implant insertion.

The error reducing measuring device can be used generally during intra-operation to help surgeons accurately determine the length of the orthopedic implant needed to address a fracture that is present in an affected bone. The error reducing measurement device has a cannulated body with a first end and a second end wherein the first end includes an undercut for measurement error reducing purposes. The error reducing measurement device may also have an elongated opening on the body with a series of markings disposed along the length of the opening for determining implant length measurements.

BRIEF DESCRIPTION OF THE DRAWINGS

Preferred features of the present invention are disclosed in the accompanying drawings, wherein similar reference characters denote similar elements throughout the several views, and wherein:

FIG. 13 is a partial cross-sectional side view of a guide sleeve according to the present invention;

FIG. 14 is a side view of the guide sleeve of FIG. 13;

FIG. 15 is a side view of an embodiment of a compression nut according to the present invention with a portion of the device shown in cross section;

FIG. 16 is a front view of the compression nut of FIG. 15;

FIG. 17 is a side view of a coupling screw according to the present invention;

FIG. 18 is a side view of a drive shaft according to the present invention;

FIG. 19 is a front view of an alignment indicator according to the present invention;

FIG. 20 is a cross-sectional side view of the handle cover according to the present invention;

DETAILED DESCRIPTION OF THE PREFERRED EMBODIMENTS

Figure 1:
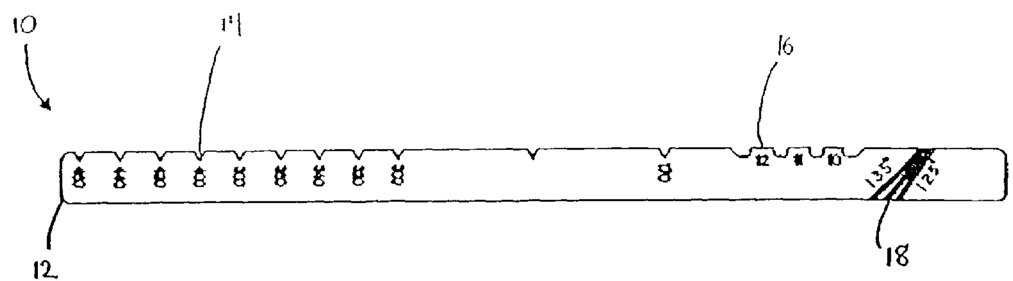
FIG. 1 is a perspective view of an embodiment of the measuring device according to the present invention.

FIG. 1 shows an exemplary embodiment of a measuring device used with the orthopedic implant insertion instruments of the present invention. Measuring device 10 can be used generally during pre-operation or intra-operation to help surgeons determine the dimensions of the orthopedic implant needed to address a fracture or impending fracture that may be present in an affected bone. Measuring device 10 can further help surgeons determine additional orthopedic measurements such as relative bone fragment angles and, in the case of bones like the femur, the angle of the femoral neck or the angle of equivalent bony structure. Generally speaking, measuring device 10 comprises elongated body 12, which is made of a radiopaque material. In a preferred embodiment, located along a partial length of body 12 are a series of spaced notches 14 with corresponding numerical designations that assist surgeons in determining the length of an implant needed to address a bone fracture. In an exemplary use, under fluoroscopic or similar radiographic conditions, one end of body 12 is aligned with a proximal portion of the fractured bone. A fluoroscopic or radiographic image is taken at a distal end of the fractured bone and the closest numerical designation in the series of spaced notches 14 on body 12 that is disposed over the distal end of the bone represents the length of the implant to be used for addressing the fractured bone.

Also located along a partial length of body 12, in a preferred embodiment, are a second series of spaced tabs 16 with a different set of corresponding numerals that assist the surgeon in determining the diameter of an implant that may be used to address a bone fracture. In an exemplary use, under fluoroscopic or radiographic conditions, body 12 is aligned transversely with a fractured bone, such as the femur. A fluoroscopic or radiographic image is taken along the medullary canal of the fractured bone, and the corresponding numerical designation of the tab in the series of spaced tabs 16 on body 12 that best covers the medullary canal represents the diameter of the implant to be used.

Figure 2:
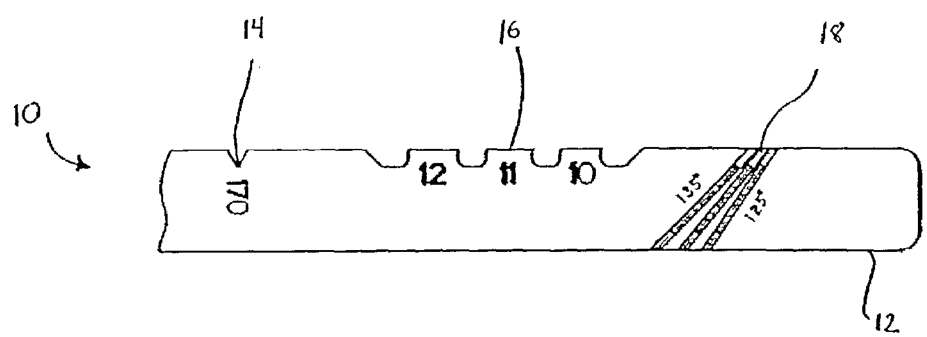
FIG. 2 is a detailed perspective view of the measuring device of FIG. 1.

As shown in FIGS. 1 and 2, in a preferred embodiment, disposed across one end of body 12 are a series of numerically labeled slots with grooves 18 placed at varying angles that assist the surgeon in determining the angle of projecting bony structures, such as the femoral neck on a femur. In an exemplary use, under fluoroscopic or radiographic conditions, measurement instrument 10 is placed over the fractured bone and aligned with the bone shaft axis. The slots in the series of slots 18 that best lines up with the axis of the bony projection corresponds to the angle of the projection. For example, on the femur, the slots in the series of slots 18 that best lines up with the axis of the femoral neck axis, indicates the femoral neck angle. To further increase the accuracy of determining the angle of a bony projection, wires can be attached within grooves 18 and aligned with the bony projection to more precisely determine the angle of the bony projection. This measurement can be used to determine the angle of insertion of a fixation implant into the bony projection or bone.

Figure 3:
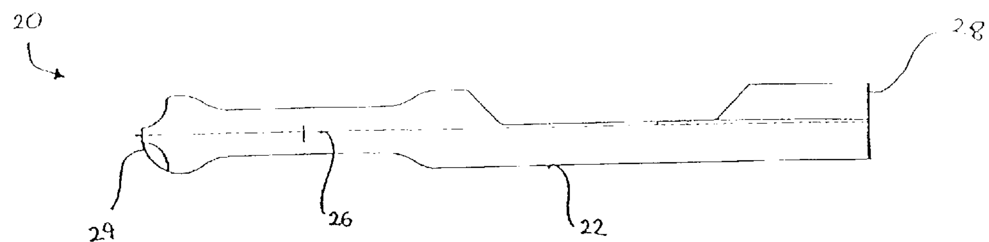
FIG. 3 is a side view of an embodiment of the error reducing measuring device according to the present invention.
Figure 4:
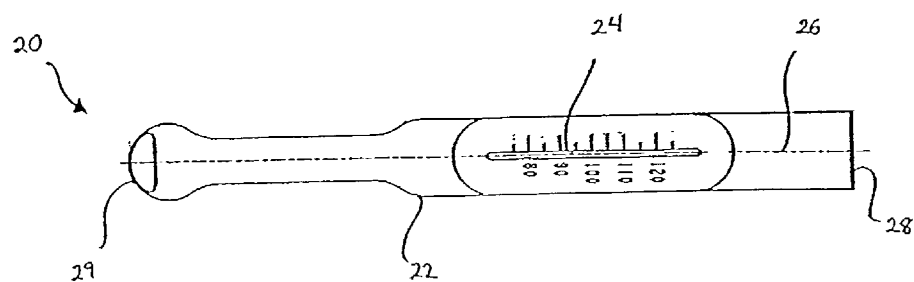
FIG. 4 is a top view of the error reducing measuring device of FIG. 3.
Figure 5:
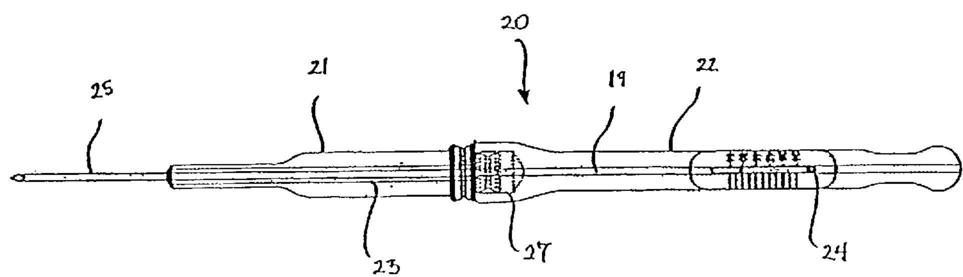
FIG. 5 is a top view of the error reducing measuring device of FIG. 3 in use with a soft tissue protection sleeve, a wire guide and a guide wire.

FIGS. 3, 4 and 5 show a preferred embodiment of an error reducing measuring device used with the orthopedic implant insertion instruments of the present invention. Error reducing measuring device 20 can be used generally during intra-operation to help surgeons accurately determine the length of the orthopedic implant needed to address a fracture that is present in an affected bone. Generally speaking, measuring device 20 comprises cannulated body 22, which is made of a biocompatible material such as metal or plastic. Body 22 has a first end 29, a second end 28, and a cannulation 19 which extends along longitudinal axis 26. In a preferred embodiment, located near second end 28, along longitudinal axis 26, is an elongated opening 24. Opening 24 offers visual access to the cannulation and has a series of scaled markings located along its length. Measuring device 20 also has an undercut 27, which can best be seen in FIG. 5, extending into body 22 at second end 28. Undercut 27 helps minimize user error, as will be explained below.

Referring now to FIG. 5, measuring device 20 is shown with wire guide 23, soft tissue protection sleeve 21 and guide wire 25. In a preferred use, soft tissue protection sleeve 21 is advanced to abut the surface of the cortex of the fractured bone. Wire guide 23 is concentrically placed within soft tissue protection sleeve 21. Since wire guide 23 has an outer diameter that approximates the inner diameter of soft tissue protection sleeve 21 and an inner diameter that approximates the diameter of guide wire 25, wire guide 23 permits guide wire 25 to be more accurately centered within soft tissue protection sleeve 21 allowing for a more accurate measurement. Guide wire 25, which has a known length, is then inserted through wire guide 23 and soft tissue protection sleeve 21 into the fractured bone. The length of guide wire 25 will be such that a portion of guide wire 25 will extend beyond the soft tissue protection sleeve 21 and the wire guide 23.

Measuring device 20 is advanced over the portion of guide wire 25 that extends outwardly from soft tissue protection sleeve 21 and wire guide 23 until measuring device 20 abuts the end of soft tissue protection sleeve 21. Undercut 27 allows second end 28 of measuring device 20 to fit around wire guide 23 thereby permitting measuring device 20 to abut only soft tissue protection sleeve 21. By abutting against only the soft tissue protection sleeve 21, wire guide 23 will not interfere with the implant measurements, thus, minimizing user error and allowing for a more accurate and reliable measurement.

Measurements are obtained via the markings disposed alongside opening 24. Guide wire 25 fits within cannulation 19 located in body 22 of measuring device 20 and is viewable through opening 24. Generally, the end of guide wire 25 is located somewhere within opening 24. The marking or measurement closest to the end of guide wire 25 is used to determine the length of the implant needed to address the fracture in the bone.

Figure 6:
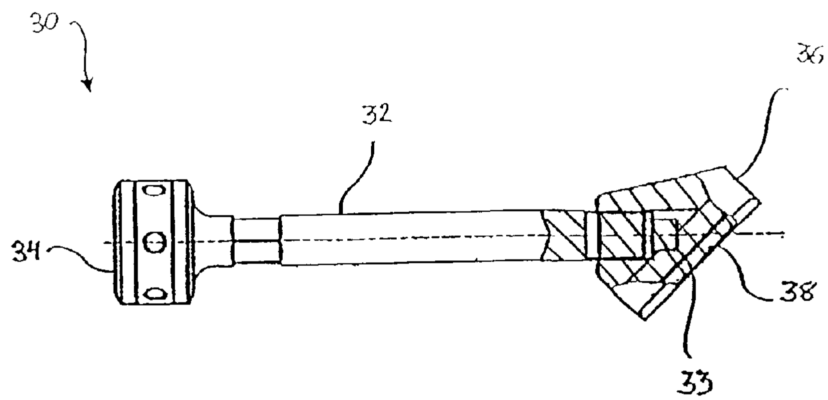
FIG. 6 is a side view of an embodiment of a striking member/soft tissue clearance device according to the present invention with a portion of the device shown in cross section.
Figure 7:
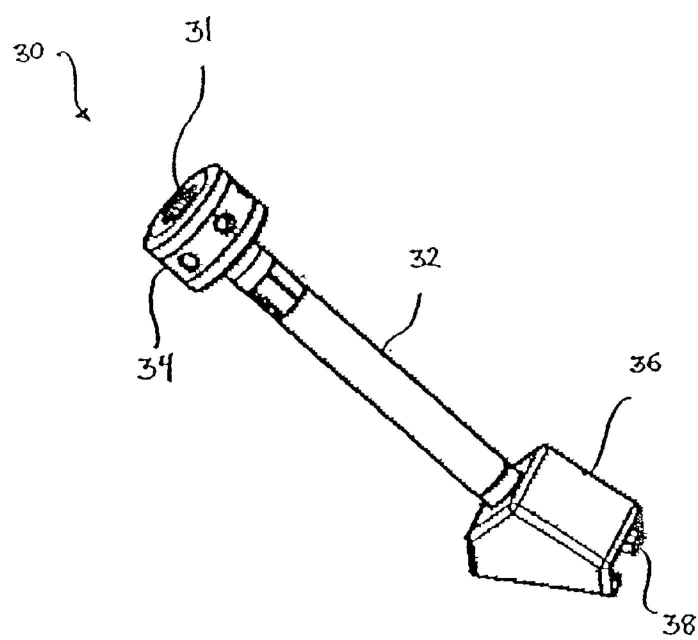
FIG. 7 is a perspective view of the striking member/soft tissue clearance device of FIG. 6.

FIGS. 6 and 7 illustrate an exemplary embodiment of a striking member/soft tissue clearance device used with the orthopedic implant insertion instruments of the present invention. Striking member/Clearance device 30 can be used generally during intra-operation to help surgeons apply an impact force to an implant insertion handle helping to drive an implant further into a bone by providing a large impact site clear of any soft tissue. Generally speaking, striking member/clearance device 30 comprises an elongated shaft 32, a base member 36, and a head 34, all of which, preferably, are made of a biocomparible material.

In a preferred embodiment, head 34 has a large, substantially flat top surface which provides the surgeon with a large impact area. Head 34 may also have internal thread 31 for the attachment of a guided slide hammer which allows the surgeon to have a more efficient, controlled impact on the clearance device 30. In a preferred embodiment, the guided slide hammer may also be used by the surgeon to pull the implant insertion handle outwardly, if necessary. This may be useful in a situation where the implant and/or the insertion handle has been driven too far into a bone.

In an exemplary embodiment, base member 36 has a pair of spaced lips 38 for sliding engagement with grooves on an implant insertion handle. For example, lips 38 can be slidingly engaged with grooves 48 on insertion handle 40 (shown in FIGS. 8 and 9). In addition, shaft 32 may be rotationally engaged to base member 36. As a result, clearance device 30 can be attached to an implant insertion handle quickly, easily and firmly by engaging lips 38 with grooves on an insertion handle and slightly turning shaft 32. Turning shaft 32 causes shaft end 33 to push against the body of an implant insertion handle thereby moving base 36 upwards and pressing lips 38 against the upper groove edges on the implant insertion handle, creating a friction lock. To unlock clearance device 30, shaft 32 is turned in the opposite direction, removing the friction lock, allowing clearance device 30 to be slidably removed from the implant insertion handle. Other methods of attaching clearance device 30 to an implant insertion handle have also been contemplated and would be readily appreciated by those skilled in the art. For example, clearance device 30 can be threadably attached to an implant insertion handle without the use of base 33 or clearance device 30 can be just slideably attached to an implant insertion handle without the need for a rotatable shaft which creates a friction lock.

Figure 8:
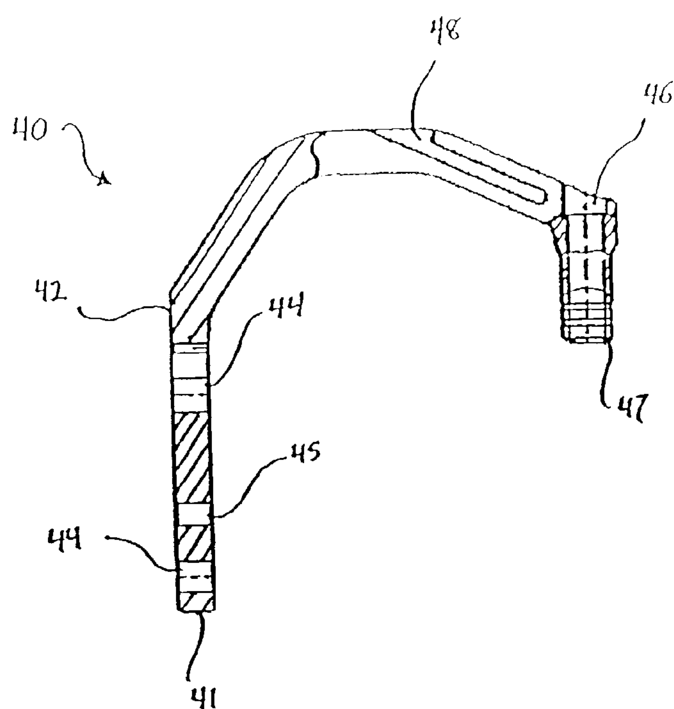
FIG. 8 is a side view of an embodiment of the implant insertion handle according to the present invention with a portion of the device shown in cross section.
Figure 9:
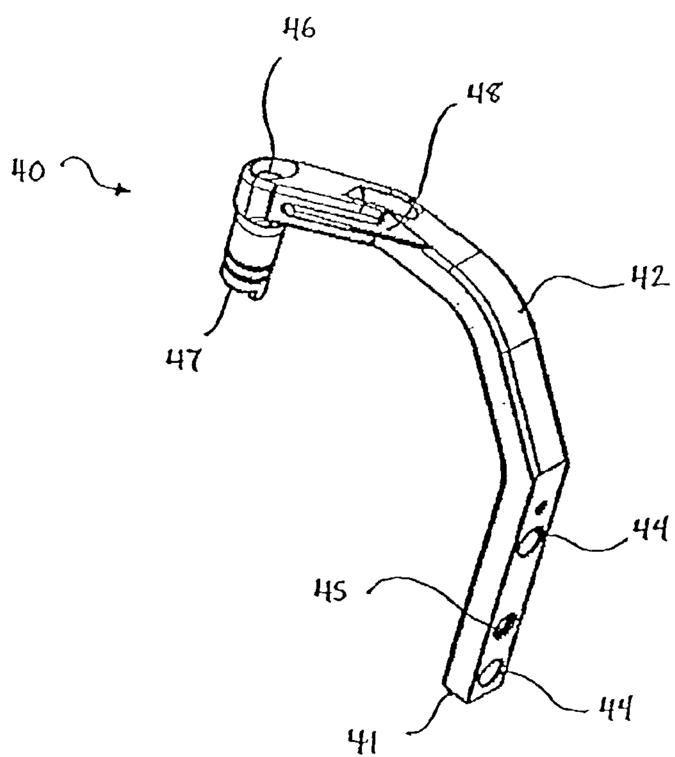
FIG. 9 is a perspective view of the implant insertion handle of FIG. 8.

FIGS. 8 and 9 show a preferred embodiment of an implant insertion handle used with the orthopedic implant insertion instruments of the present invention. In general, implant insertion handle 40 is used during the orthopedic procedure to insert a fixation implant, such as an intramedullary nail, into a bone, such as a femur, and to connect to other implant insertion instruments, such as an aiming arm. In a preferred embodiment, insertion handle 40 comprises a curved body 42 preferably made of a biocompatible material having a first end 41 and a second end 47. In an exemplary embodiment, second end 47 connects to a fixation implant, such as the intramedullary nail 120 (shown in FIG. 21) via a connection member (not shown), such as a screw or bolt, inserted through bore 46. Grooves 48 may be located, preferably, along an upper portion of body 42 and are used for attaching a soft tissue clearance device, such as device 30, as explained above. Preferably, located near first end 41, are at least one alignment hole 44 and a threaded bore 45. Alignment holes 44 and threaded bore 45 align and connect insertion handle 40 to another insertion instrument, such as aiming arm 50 (shown in FIGS. 10–12).

Figure 10:
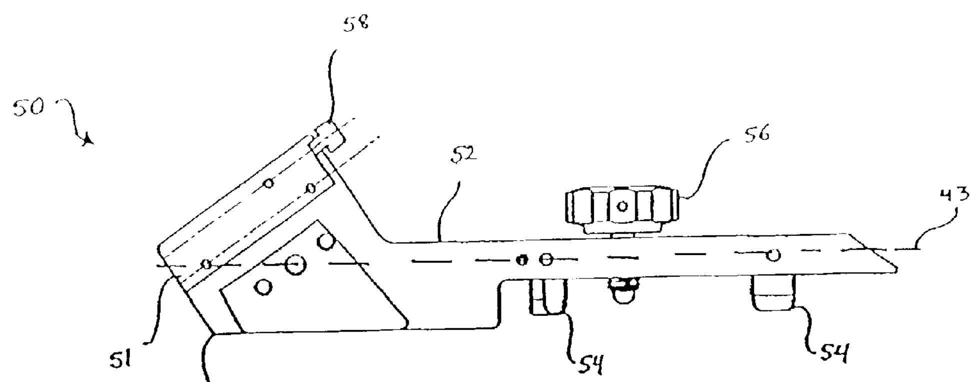
FIG. 10 is a side view of an aiming arm according to the present invention.
Figure 11:
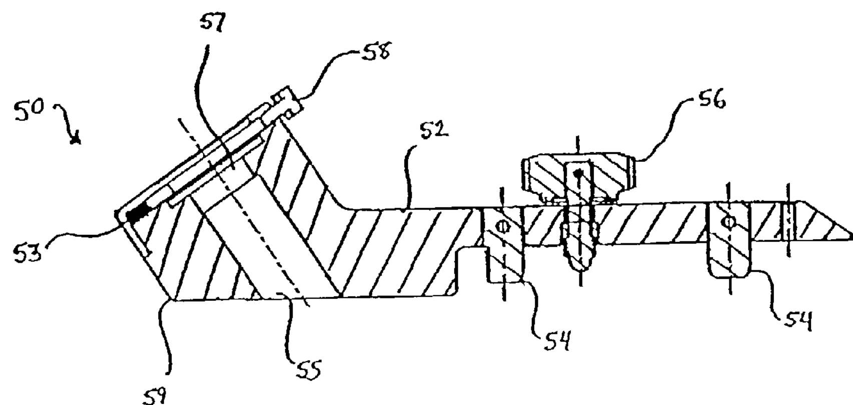
FIG. 11 is a cross-sectional side view of the aiming arm shown in FIG. 10.
Figure 12:
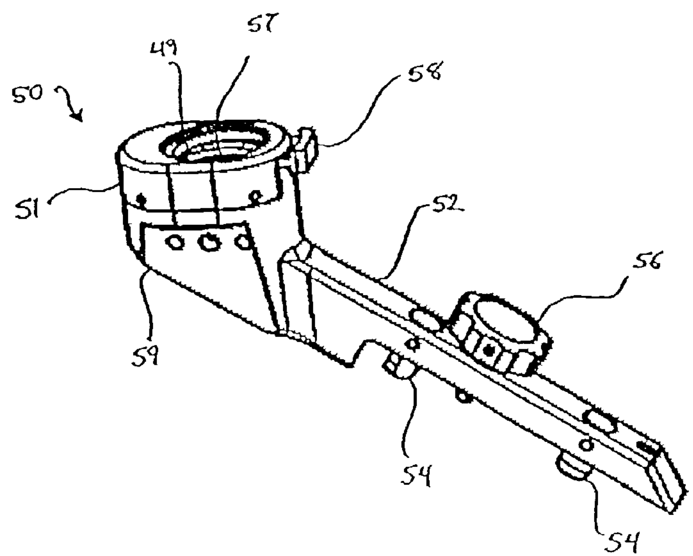
FIG. 12 is a perspective view of the aiming arm of FIG. 10.
Figure 21:
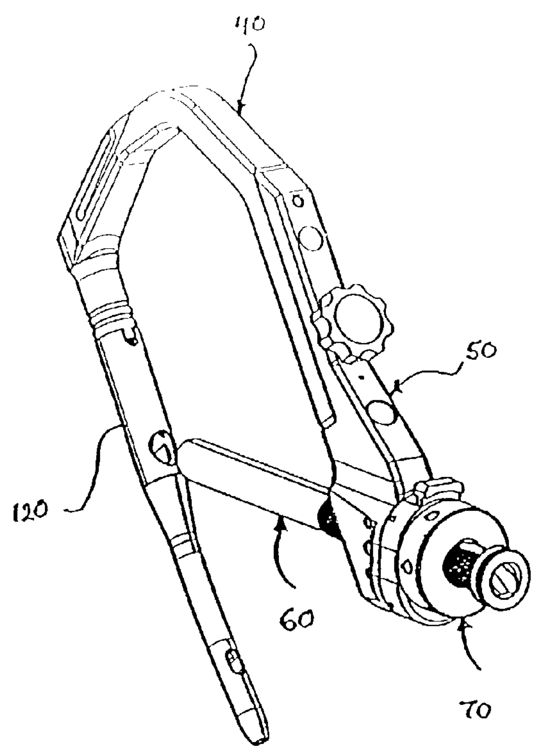
FIG. 21 is a perspective view of the aiming arm of FIG. 10, the implant insertion handle of FIG. 8, the compression nut of FIG. 15, and the guide sleeve of FIG. 13 assembled together and in use with an intramedullary nail.

FIGS. 10, 11, and 12 illustrate a preferred embodiment of an aiming arm used with the orthopedic implant insertion instruments of the present invention. Generally speaking, aiming arm 50 is used during orthopedic surgery as an aiming structure for precise positioning of a locking implant, such as a helical blade or lag screw. In an exemplary embodiment, aiming arm 50 comprises body 52 preferably made from a biocompatible material. Extending from body 52 may be at least one alignment pin 54 which cooperates with at least one alignment hole 44 located in body 42 of insertion handle 40. Alignment pins 54 and alignment holes 44 permit aiming arm 50 to precisely and accurately align with insertion handle 40. Also extending from body 52 is attachment member 56. Attachment member 56 extends through body 52 and once insertion handle 40 and aiming arm 50 are sufficiently aligned, attachment member 56 is threadably advanced into threaded bore 45 locking insertion handle 40 and aiming arm 50 together. FIG. 21 shows insertion handle 40 coupled to aiming arm 50. Although attachment member 56 is preferably a threaded shaft with a contoured knob, other embodiments have been contemplated and would be readily appreciated to those skilled in the art. For example, attachment member 56 can be a screw or a bolt with a tool engaging slot.

In a preferred embodiment, body 52 further includes sleeve retaining portion 59 which is the angled portion of body 52. Sleeve retaining portion 59 has a channel 55 which receives a guide sleeve or other guidance assembly to be described below. Sleeve retaining portion 59, and channel 55, are angled with respect to longitudinal axis 43 to align the guide sleeve or other guidance assembly with a portion of the fractured bone that need to be addressed. In addition, if a fixation implant is already seated in the bone, sleeve retaining portion 59, and channel 55, are angled to align the guide sleeve or other guidance assembly with a locking hole that is typically present in the fixation implant. This allows for a second implant, such as a locking implant, as disclosed in U.S. patent application Ser. No. 09/978,002 entitled "Bone Fixation System", the entire contents of which is expressly incorporated herein, to be implanted with the assistance of the guide sleeve or other guidance assembly into the bone via the locking hole in the already seated fixation implant. Since sleeve retaining portion 59 of aiming arm 50 needs to be angled with respect to longitudinal axis 43 at an angle which correspond to the angle needed to address the bone as well as an angle to align with a locking hole in a fixation implant, aiming arm 50 will be available, preferably, in different embodiments, each having a sleeve retaining portion 59 angled at a different angle with respect to longitudinal axis 43.

For example, in the case of a fracture in the neck and/or body of a femur, an intramedullary nail will be first inserted into the medullary canal of the femur with the aid of insertion handle 40 and soft tissue clearance device 30 to address the fracture in the body of the femur. Alternatively, the intramedullary nail may have been present in the medullary canal from a previous surgical implantation. A second implant in the form of a locking implant should then be inserted through the locking hole of the intramedullary nail and into the neck of the femur to address the femoral fracture. In order to properly implant the locking implant, the locking implant must be correctly aligned with the femoral neck and the locking hole in the intramedullary nail before the locking implant is implanted. Aiming arm 50, and more specifically sleeve retaining portion 59 with channel 55, is used to align the locking implant. Aiming arm 50, which is aligned with and coupled to insertion handle 40, via sleeve retaining portion 59, is chosen to orient the locking implant so that it aligns with the locking hole in the intramedullary nail as well as the femoral neck when it is implanted. Typically, the locking hole in the intramedullary nail will have an angle designation between 125° to 135°, which corresponds to the femoral neck angle. Accordingly, aiming arm 50 with the correct sleeve retaining portion 59 will be chosen to match that angle designation. As a result, the locking implant will be properly oriented and angled when it is implanted through the locking hole in the intramedullary nail and into the femoral neck.

Referring to FIG. 11, in a preferred embodiment, sleeve retaining portion 59 has a D-shaped opening 57 and a channel 55 that retains the guide sleeve or similar instrument. Opening 57 is, preferably, D-shaped to prevent rotation of the sleeve relative to aiming arm 50 once it is inserted into retaining portion 59. Although in an exemplary embodiment, opening 57 is D-shaped, any shape or structure may be used, preferably, a shape to prevent the sleeve from rotating with respect to aiming arm 50. For example, a groove can be introduced on the outer surface of the guide sleeve and channel 55 can have a pin which mates with the groove preventing rotation of the guide sleeve with respect to aiming arm 50.

Referring now to FIGS. 10 and 11, located at opening 57 is engagement member 58 and biasing member 53. In an exemplary embodiment, engagement member 58 is a thin plate having an opening 49, which is preferably oval. Opening 49 in engagement member 58 is resiliently offset with respect to channel 55 and opening 57 by biasing member 53. In a preferred embodiment, biasing member 53 is a spring. Cover portion 51 is attached to body 52 and serves to contain biasing member 53 and engagement member 58. Engagement member 58 is designed to retain compression nut 70 (shown in FIG. 15) while allowing the compression nut to rotate with respect to aiming arm 50. The purpose of allowing compression nut 70 to rotate will be explained below.

FIGS. 13 and 14 show a preferred embodiment of the guide sleeve used with the aiming arm 50, and more specifically with sleeve retaining portion 59 of aiming arm 50 as described below. Generally speaking, guide sleeve 60 is used during orthopedic surgery to align and guide the locking implant, such as a helical blade or lag screw, and to protect surrounding soft tissue when a locking implant is implanted into a bone. Advantageously, guide sleeve 60 also precisely controls the rotational and translational positioning of the inserted locking implant. In an exemplary embodiment, guide sleeve 60 comprises tubular body 62 made from a biocompatible material having a first end 65, a second end 61, and a central bore 69. In addition, body 62, preferably, has a flat 64 running along its length, effectively changing the cross-sectional shape of body 62 from circular to substantially D-shaped. Although in an exemplary embodiment, guide sleeve 60 has a D-shaped cross-section, any cross-sectional shape may be used and it is preferred that the shape is such that it will not allow guide sleeve 60 to rotate with respect to aiming arm 50. Located at second end 61 may be shoulder 63 and in an exemplary embodiment, body 62 also has threading 66 disposed on the outer surface of body 62, preferably running partially along the length of body 62.

Central bore 69 runs along the entire length of guide sleeve 60 and is the passageway used to guide the locking implant. In a preferred embodiment, located along the periphery of central bore 69 is at least one helically oriented groove 68. Groove 68 is designed to control the rotational and translational movements of the locking implant driving instruments and locking implant. In a preferred embodiment, there are three grooves 68, but any number of grooves may be used to control the rotational and translational movements of the locking implant driving instruments and locking implant. Groove 68 is designed such that each full rotation of groove 68 will equate to a predetermined amount of translational distance along the longitudinal axis of guide sleeve 60. This allows for translational control of the locking implant driving instrument and locking implant.

Furthermore, groove 68 is designed such that the beginning and end of groove 68 correspond to predetermined rotational positions for the locking implant driving instruments and locking implant, and the pitch of groove 68 determines the amount of rotation the locking implant and locking implant driving instruments will undergo when moving from the beginning to the end of groove 68. This allows for rotational control of the locking implant driving instrument and locking implant. By having rotational control, the rotational orientation of the locking implant can be determined throughout the implantation and after the locking implant is seated, thereby allowing the locking implant to be rotationally aligned within the fracture and to be rotationally aligned to another fixation implant. For example, in the case of the helical blade or lag screw and the intramedullary nail, by having rotational control of the helical blade or lag screw, the rotational position and orientation of the helical blade or lag screw can be determined with respect to the intramedullary nail allowing the helical blade or lag screw to be fixed to the intramedullary nail, if necessary. By having translational control, the distance the locking implant needs to travel and depth the implant needs to be inserted can be controlled so that the locking implant travels the correct distance and is seated at the correct depth.

FIGS. 15 and 16 illustrate an exemplary embodiment of a compression nut used with guide sleeve 60 and aiming arm 50. In general, compression nut 70 is used during orthopedic surgery to restrict the insertion depth of a locking implant, such as a helical blade or lag screw, and to provide compression or reduction to a fracture. In an exemplary embodiment, compression nut 70 comprises an annular body 72 made from a biocompatible material having a first end 71, an extension 75 with a second end 73, and a central bore 74. In a preferred embodiment, central bore 74 is threaded to threadably attach to guide sleeve 60. The outer surface of body 72 may also be knurled to improve the user's grip on the nut when it is turned.

Referring to FIG. 15, second end 73 of extension 75 has flange 76 extending around its periphery. Flange 76 and extension 75 engage engagement member 58 of aiming arm 50, locking compression nut 70 with aiming arm 50, but still allowing compression nut 70 to rotate with respect to aiming arm 50.

Turning to FIG. 21, in an exemplary embodiment, compression nut 70 is threaded onto guide sleeve 60. Guide sleeve 60 is then advanced through sleeve retaining portion 59 of aiming arm 50 until compression nut 70 engages sleeve retaining portion 59. Compression nut 70 engages sleeve retaining portion 59 when flange 76 pushes against the edge of the opening 49 of engagement member 58, pushing engagement member 58 against resilient member 53, and lining up the opening 49 in engagement member 58 with opening 57 and channel 55. Extension 75 along with flange 76 are then advanced through the opening 49 in engagement member 58. Since the diameter of extension 75 is less than the diameter of second end 73 with flange 76, engagement member 58 is resiliently biased back to the resiliently offset position by resilient member 53, when flange 76 passes through the opening 49 in engagement member 58. This results in engagement member 58 locking compression nut 70 to aiming arm 50 but still allowing engagement nut 70 to rotate with respect to aiming arm 50.

Once engaged to aiming arm 50, compression nut 70 can be used to control the insertion depth of a locking implant. In the embodiment shown, since compression nut 70 is engaged to aiming arm 50 and is threadably attached to guide sleeve 60, rotation of compression nut 70 results in translation of guide sleeve 60 with respect to aiming arm 50 since guide sleeve 60 is slideably retained in guide sleeve retaining portion 59 of aiming arm 50 and guide sleeve 60 cannot rotate with respect to aiming arm 50. Thus, by rotating compression nut 70 in one direction, the end 65 of guide sleeve 60 will move further out from aiming arm 50 and away from the bone. This results in a lesser insertion depth for the locking implant because shoulder 63 on guide sleeve 60 will abut the locking implant driving instrument at a greater distance from the bone allowing for only a shallower insertion depth for the implant. By rotating compression nut 70 in the opposite direction, guide sleeve 60 will move further into aiming arm 50 and toward the bone. This results in a greater insertion depth for the locking implant because although shoulder 63 will abut the locking implant driving instruments, the locking implant driving instruments will abut shoulder 63 at a lesser distance from the bone fracture allowing for a deeper insertion depth for the implant.

Compression nut 70 can also be used to compress or reduce a fracture. In the situation where a locking implant, such as a helical blade or lag screw, has been inserted into the fractured bone across the fracture site, but is still connected to the locking implant driving instruments, rotating compression nut 70 will cause the guide sleeve 60 to move further out from aiming arm 50. This will cause the locking implant driving instruments, which are coupled to guide sleeve 60, to move further out pulling the locking implant in an outward direction without rotating the locking implant. This results in the locking implant pulling on the fractured bone thereby reducing the fracture gap and compressing the fracture fragments.

FIGS. 17, 18, 19, 20, and 22 illustrate a preferred embodiment of the locking implant driving instruments. FIG. 17 shows an exemplary embodiment of a coupling screw used during orthopedic surgery to couple to a locking implant and help drive the locking implant into the bone. In general, coupling screw 80 is made from a biocompatible material and comprises body 82 which has a first end 81 and a second end 83. In a preferred embodiment, located at first end 81 is a large, knurled knob 86 which is used by a surgeon to turn coupling screw 80. Located at second end 83 is threading 84 which is used to threadably attach a locking implant to coupling screw 80. Although in the preferred embodiment, the locking implant is coupled to coupling screw 80 by way of threading, other ways of coupling, such as an interference fit, may also be used. Coupling screw 80 may also be cannulated to allow for the passage of a guide wire.

Figure 22:
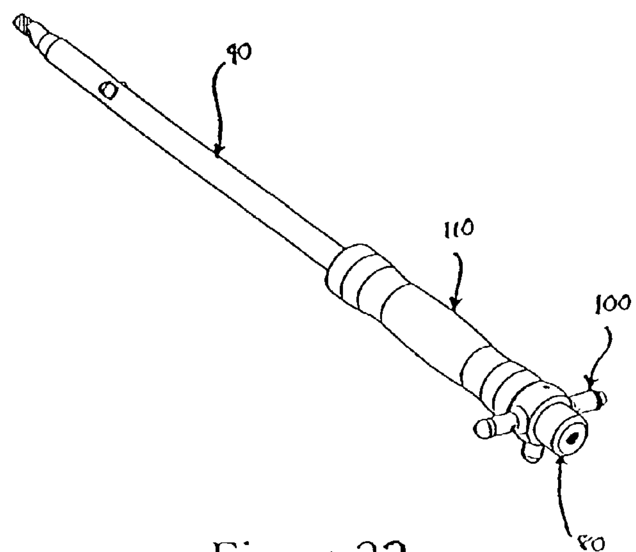
FIG. 22 is a perspective view of the coupling screw of FIG. 17, the drive shaft of FIG. 18, the alignment indicator of FIG. 19, and the handle cover of FIG. 20 assembled together.

FIG. 18 shows a preferred embodiment of a drive shaft used during orthopedic surgery to couple to a locking implant and help drive the locking implant into the bone. Generally speaking, drive shaft 90 is made from a biocompatible material and comprises cannulated body 92 which has a first end 91 and a second end 93. Body 92 is cannulated to allow coupling screw 80 to be slideable advanced into drive shaft 90 as shown in FIG. 22. In an exemplary embodiment, located at second end 93 are prongs 96 which are also used to couple to the locking implant. Also located along body 92 is shoulder 98. Shoulder 98 is used, as explained above, to abut against shoulder 63 of guide sleeve 60 to limit the insertion depth of drive shaft 90 in guide sleeve 60. By limiting the insertion depth of drive shaft 90, the insertion depth of the locking implant is limited thereby preventing the surgeon from inserting and seating the locking implant incorrectly in the fractured bone.

In an exemplary embodiment, body 92 of drive shaft 90 has at least one pin 94. Pin 94 cooperates with groove 68 in guide sleeve 60 to allow rotational and translational control of the locking implant and locking implant driving instruments. The number of pins 94 preferably correspond to the number of grooves 68. Therefore, if there are three grooves 68 in guide sleeve 60, there preferably will be three pins 94 on body 92 of drive shaft 90.

In a preferred use of the locking implant driving instruments, coupling screw 80 is slideably advanced through drive shaft 90. An alignment indicator 100 and handle cover 110 may be optionally used with coupling screw 80 and drive shaft 90 and are explained below. A locking implant is then attached to coupling screw 80 via threading 84 and drive shaft 90 via prongs 96. Coupling screw 80 and drive shaft 90, with a locking implant, are then introduced into guide sleeve 60 at second end 61. As the assembly is advanced into central bore 69 of guide sleeve 60, pins 94 on drive shaft 90 engage grooves 68 in guide sleeve 60. Grooves 68 control the rotational and translational movement of the locking implant driving instruments and locking implant through pins 94. Therefore, as the locking implant driving instruments are advanced through guide sleeve 60, they will rotate and translate according to the location and pitch of grooves 68. It is readily appreciated by one skilled in the art that the location of at least one pin 94 and at least one groove 68 may interchanged. Thus, instead of having at least one pin 94 extending from body 92 of drive shaft 90, body 92 may have one or more grooves and guide sleeve 60, instead of having at least one groove 68 in central bore 69, may have one or more inwardly extending pins in central bore 69 of guide sleeve 60.

Figure 18A:
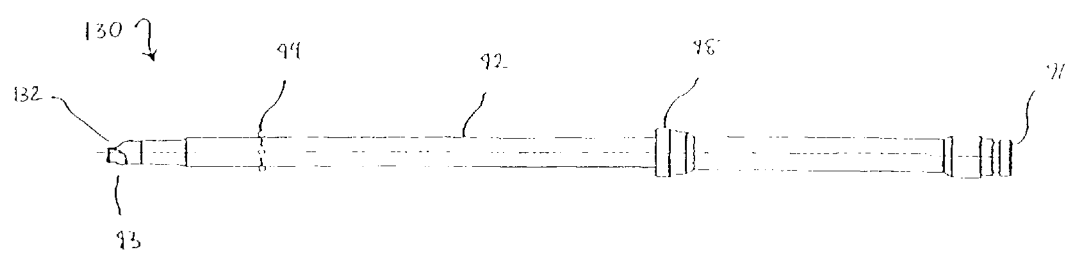
FIG. 18A is a side view of another embodiment of a drive shaft according to the present invention.

FIG. 18A shows another exemplary preferred embodiment of a drive shaft 130 used during orthopedic surgery to couple to a locking implant and help drive the locking implant into the bone. In general, most of the structure of drive shaft 130 is similar or comparable to the structure of drive shaft 90. Accordingly, the equivalent structures of drive shaft 130 have been numbered the same as drive shaft 90 and discussion of the similar components and features is not believed necessary. In this particular embodiment, at second end 93 of drive shaft 130, instead of having prongs 96, drive shaft 130 has a male projection 132 designed to operatively interface with a female portion located on the locking implant to provide rotational and translational movement to the locking implant. However, it can be readily appreciated by one skilled in the art, that drive shaft 130 may, instead, have the female portion while the locking implant may have the male projection. Furthermore, male projection 132 may be any shape that engages and transmits rotational movement to the locking implant. For example, male projection 132 may have a D-shape or may have a rectangular shape.

FIGS. 19 and 20 respectively show preferred embodiments of an alignment indicator and handle cover used during orthopedic surgery. Alignment indicator 100 has legs 102 a central bore 104 and, optionally, an interference fit pin 106. Alignment indicator 100 is coupled, preferably through an interference fit, to body 92 of drive shaft 90 near first end 91 via central bore 104 and pin 106. Alignment indicator 100 is used to indicate the rotational orientation of the locking implant during the insertion process. As the locking implant and the locking implant driving instruments rotate during insertion, alignment indicator 100 also rotates. The orientation of legs 102 at any given point during the insertion process when compared to their starting orientation, will indicate the rotational orientation of the locking implant. FIG. 22 shows alignment indicator 100 coupled to drive shaft 90.

Handle cover 110 has a tubular body 112 having a first end 114, a second end 116, and a bore 118. Handle cover 110 fits over drive shaft 90 as shown in FIG. 22. In a preferred embodiment, handle cover 110 is contoured for easy gripping by the surgeon and rotates independently of drive shaft 90. This allows the surgeon to easily hold the locking implant insertion instruments while they rotate during the implant insertion process.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. An orthopedic implant insertion assembly for inserting an implant, comprising:

a handle member having an arcuate body with a first end and a second end, the first end of the handle configured and designed to couple to the implant;

at least one arm member having a longitudinal axis, a first end and a second end, the first end of the arm member having at least one attachment member configured and designed to couple to the second end of the handle member and the second end of the arm member having a sleeve retaining portion wherein the sleeve retaining portion has a channel that is angled with respect to the longitudinal axis; and a nut member having a bore for coupling to an insertion instrument and having a flange member for coupling to the sleeve retaining portion of the arm member wherein the arm member further comprises a resiliently biased engagement member located on the sleeve retaining portion for engaging an insertion instrument.

2. An orthopedic implant insertion assembly for inserting an implant, comprising:

a handle member having an arcuate body with a first end and a second end, the first end of the handle configured and designed to couple to the implant;

at least one arm member having a longitudinal axis, a first end and a second end, the first end of the arm member having at least one attachment member configured and designed to couple to the second end of the handle member and the second end of the arm member having a sleeve retaining portion wherein the sleeve retaining portion has a channel that is angled with respect to the longitudinal axis;

a nut member having a bore for coupling to an insertion instrument and having a flange member for coupling to the sleeve retaining portion of the arm member; and a sleeve member having a central bore, the central bore having either at least one helically oriented groove extending substantially along the length of the central bore or at least one inwardly extending pin.

3. The orthopedic implant insertion assembly of claim 2, wherein the sleeve member is configured and dimensioned for slideable insertion with the channel of the arm member and wherein the sleeve member has a substantially non-circular cross-section.

4. An orthopedic implant insertion assembly for inserting an implant, comprising:

a handle member having an arcuate body with a first end and a second end, the first end of the handle configured and designed to couple to the implant;

at least one arm member having a longitudinal axis, a first end and a second end, the first end of the arm member having at least one attachment member configured and designed to couple to the second end of the handle member and the second end of the arm member having a sleeve retaining portion wherein the sleeve retaining portion has a channel that is angled with respect to the longitudinal axis;

a nut member having a bore for coupling to an insertion instrument and having a flange member for coupling to the sleeve retaining portion of the arm member; and a sleeve member having an outer surface, the outer surface having threading disposed at least partially along the length of the sleeve member.

5. The orthopedic implant insertion assembly of claim 4, wherein the sleeve member is configured and dimensioned for slideable insertion with the channel of the arm member and wherein the sleeve member has a substantially non-circular cross-section.

6. An orthopedic implant insertion assembly for inserting an implant, comprising:

a handle member having an arcuate body with a first end and a second end, the first end of the handle configured and designed to couple to the implant at least one arm member having a longitudinal axis, a first end and a second end, the first end of the arm member having at least one attachment member configured and designed to couple to the second end of the handle member and the second end of the arm member having a sleeve retaining portion wherein the sleeve retaining portion has a channel that forms a non-straight anale with respect to the longitudinal axis; and a nut member having a threaded bore for coupling to an insertion instrument and having a flange member for coupling to the sleeve retaining portion of the arm member.

7. The orthopedic implant insertion assembly of claim 6, wherein the handle member has a bore located at the first end for receiving a connection member to couple the handle member to an implant.

8. The orthopedic implant insertion assembly of claim 6, wherein the handle member has at least one bore located at the second end for receiving the attachment member to couple the handle member to the arm member.

9. The orthopedic implant insertion assembly of claim 6, wherein the handle member further comprises at least one groove located on the arcuate body configured and designed to couple with an insertion instrument.

10. The orthopedic implant insertion assembly of claim 6, wherein the arm member further comprises at least one alignment member.

11. The orthopedic implant insertion assembly of claim 10, wherein the handle member has at least one bore located at the second end for receiving the alignment member to align the handle member with the arm member.

12. The orthopedic insertion assembly of claim 6, wherein the channel has a substantially non-circular shape.

13. The orthopedic implant insertion assembly of claim 6, wherein the nut member has an outer surface having texturing for improving grip on the nut member.

14. The orthopedic implant insertion assembly of claim 6, further comprising:

a striking member having an end cap with a shaft, wherein the shaft can be coupled to the handle member.

15. The orthopedic implant assembly of claim 6, further comprising:

at least a second arm member having a longitudinal axis, a first end and a second end, the first end of the second arm member having at least one attachment member configured and designed to couple to the second end of the handle member and the second end of the second arm member having a sleeve retaining portion wherein the sleeve retaining portion has a channel that is angled with respect to the longitudinal axis of the second arm member, the angle of channel of the first arm member with respect to its longitudinal axis being different than the angle of the channel of the second member with respect to its longitudinal axis.

16. The orthopedic implant insertion assembly of claim 6, further comprising:

a cannulated drive shaft having a first end and a second end, and having an attachment structure located at either the first end or the second end for attachment to the implant; and a coupling member having an elongated body with a coupling structure disposed on one end for coupling to the implant and a head disposed on the other end for gripping and rotating the coupling member, wherein the coupling member is configured and dimensioned for slideable insertion within the drive shaft.

17. The orthopedic implant insertion assembly of claim 16, wherein the drive shaft further comprises at least one outwardly extending pin located between the first end and second end.

18. The orthopedic implant insertion assembly of claim 16, wherein the drive shaft further comprises at least one helically oriented groove extending substantially along the length of the drive shaft.

19. The orthopedic implant insertion assembly of claim 16, wherein the attachment structure comprises one of either at least one pin or at least one groove for coupling with the implant.

20. The orthopedic implant insertion assembly of claim 16, wherein the attachment structure comprises one of either a male protrusion or a female portion for coupling with the implant.

21. The orthopedic implant insertion assembly of claim 16, wherein the coupling structure comprises threading for threadably coupling with the implant.

22. The orthopedic implant insertion assembly of claim 16, wherein the drive shaft further comprises an outwardly extending shoulder located between the first end and the second end for limiting the insertion depth of the implant.

23. The orthopedic implant insertion assembly of claim 16, further comprising:

a handle cover having a first end, a second end and a central bore, the central bore is configured and dimensioned to slideably and rotatably receive the drive shaft for allowing the drive shaft to rotate with respect to the handle cover.

24. The orthopedic implant insertion assembly of claim 16, further comprising: an alignment indicator for coupling to the drive shaft for determining rotational orientation of the drive shaft.

25. The orthopedic implant insertion assembly of claim 6, further comprising a measurement device, the measurement device comprising an elongated body having a set of scaled notches disposed partially along a side of the body for determining the appropriate implant length, a set of scaled tabs disposed partially along a side of the body for determining the appropriate implant diameter and having an angled set of slots with grooves disposed across the body for determining the appropriate implant insertion angle.

26. The orthopedic insertion assembly of claim 6, wherein the arm member further comprises a resiliently biased engagement member located on the sleeve retaining portion for engaging an insertion instrument.

27. The orthopedic implant insertion assembly of claim 6, further comprising: a sleeve member having a central bore, the central bore having either at least one helically oriented groove extending substantially along the length of the central bore or at least one inwardly extending pin.

28. The orthopedic implant insertion assembly of claim 6, further comprising: a sleeve member having an outer surface, the outer surface having threading disposed at least partially along the length of the sleeve member.

29. An orthopedic implant insertion assembly for insertion of an implant, comprising:

a handle member having an arcuate body with a first end and a second end, the first end of the handle configured and designed to couple to the implant;

a first arm member having a longitudinal axis, a first end and a second end, the first end of the arm member having at least one attachment member configured and designed to couple to the second end of the handle member and the second end of the arm member having a sleeve retaining portion wherein the sleeve retaining portion has a channel that is angled with respect to the longitudinal axis; and a second arm member having a longitudinal axis, a first end and a second end, the first end of the second arm member having at least one attachment member configured and designed to couple to the second end of the handle member and the second end of the second arm member having a sleeve retaining portion wherein the sleeve retaining portion has a channel that is angled, the angle of channel of the first arm member with respect to its longitudinal axis being different than the angle of the channel of the second member with respect to its longitudinal axis.

30. An orthopedic implant insertion kit to assist in inserting an implant, the kit, comprising:

a handle member having an arcuate body with a first end and a second end, the first end of the handle configured and designed to couple to a first portion of the implant;

a first arm member having a longitudinal axis, a first end and a second end, the first end of the arm member having at least one attachment member configured and designed to couple to the second end of the handle member and the second end of the arm member having a sleeve retaining portion wherein the sleeve retaining portion has a channel that is angled with respect to the longitudinal axis;

a nut member having a bore for coupling to an insertion instrument and having a flange member for coupling to the sleeve retaining portion of the arm member;

a sleeve member having a central bore, the sleeve member configured to be received in the channel of the first arm member;

a cannulated drive shaft having a first end and a second end, and having an attachment structure located at either the first end or the second end for attachment to a second portion of the implant, the cannulated drive shaft configured and adapted to be received in the central bore of the sleeve member; and a coupling member having an elongated body with a coupling structure disposed on one end for coupling to the second portion of the implant and a head disposed on the other end for gripping and rotating the coupling member, wherein the coupling member is configured and dimensioned for slideable insertion within the drive shaft.

* * * * *

UNITED STATES PATENT AND TRADEMARK OFFICE

CERTIFICATE OF CORRECTION

PATENT NO. : 7,175,633 B2
APPLICATION NO. : 10/269976
DATED : February 13, 2007
INVENTOR(S) : Roth et al.

It is certified that error appears in the above-identified patent and that said Letters Patent is hereby corrected as shown below:

Column 14, line 1, "portion has a channel that forms a non-straight anale" should read -- portion has a channel that forms a non-straight angle --.

Signed and Sealed this

Fourteenth Day of August, 2007

JON W. DUDAS
*Director of the United States Patent and Trademark Office*